(12) United States Patent
Shigehara et al.

(10) Patent No.: US 6,340,739 B1
(45) Date of Patent: Jan. 22, 2002

(54) POLYAMIDE AND PROCESS FOR PRODUCING THE SAME

(75) Inventors: Kiyotaka Shigehara; Yoshihiro Katayama, both of Tokyo; Seiji Nishikawa; Yasushi Hotta, both of Satte, all of (JP)

(73) Assignees: Cosmo Research Institute; Cosmo Oil Co., Ltd., both of Tokyo (JP)

( * ) Notice: Subject to any disclaimer, the term of this patent is extended or adjusted under 35 U.S.C. 154(b) by 0 days.

(21) Appl. No.: 09/673,740

(22) PCT Filed: Apr. 19, 1999

(86) PCT No.: PCT/JP99/02065

§ 371 Date: Oct. 20, 2000

§ 102(e) Date: Oct. 20, 2000

(87) PCT Pub. No.: WO99/54384

PCT Pub. Date: Oct. 28, 1999

(30) Foreign Application Priority Data

Apr. 20, 1998 (JP) ............................................. 10-109180

(51) Int. Cl.⁷ ........................ C08G 69/26; C07D 309/38
(52) U.S. Cl. ........................ 528/310; 528/170; 528/322; 528/327; 528/335; 528/336; 549/291
(58) Field of Search ................................. 528/170, 310, 528/322, 327, 335, 336; 549/291

(56) References Cited

PUBLICATIONS

Journal of Biochemistry, vol. 93, No. 2, 1983, Kiyofumi Maruyama, "Purification and Properties of 2–pyrone—4, 6–Dicarboxylate Hydrolase", p. 557, 1983. The month in the date of publication is not available.*

CA 134: 353629, Studies of polymers containing a fine–membered lactone unit in main chain VI., Kimura, Takao et al, 2001. The month in the date of publication is not available.*

* cited by examiner

Primary Examiner—P. Hampton-Hightower
(74) Attorney, Agent, or Firm—Oblon, Spivak, McClelland, Maier & Neustadt, PC

(57) ABSTRACT

A polyamide having repeating units represented by formula (1), wherein $R^1$ represents a divalent hydrocarbon residue optionally having in the structure a heteroatom having no active hydrogen. The polyamide has a high refractive index, is biodegradable, and is useful as a material for fibers and plastics.

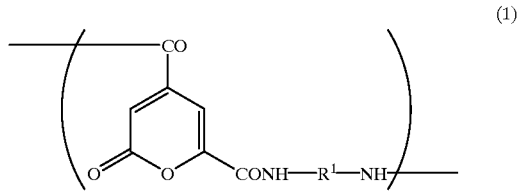

(1)

6 Claims, No Drawings

POLYAMIDE AND PROCESS FOR PRODUCING THE SAME

TECHNICAL FIELD

The present invention relates to a polyamide which has a high polarity and a high refractive index and which is useful as a material for producing fibers or plastics; to a process for producing the polyamide; and to an intermediate for producing the polyamide.

BACKGROUND ART

Examples of materials and products prepared from polyamides includes polyamide fiber such as Nylon, polyamide resin employed as engineering plastics, and aramid fiber such as Kevlar fiber. These polyamides are widely employed in such applications as general purpose fiber materials, elastic fiber materials, high-strength fiber materials, and plastics.

However, there is a demand for the development of a polyamide that exhibits enhanced properties. One example is swimwear. When white swimwear fabricated with a conventional nylon is worn, the body of the wearer can be seen through the swimwear due to the proximity of the refractive index of water and that of nylon. Meanwhile, swimwear fabricated with a conventional high-refractive-index polyamide is disadvantaged by feeling uncomfortable against the skin and by having an unsatisfactory appearance. Thus, there is a demand for a polyamide that can provide a fibersatisfying both a high refractive index and having a good sensation against the skin. In addition, conventional polyamide has poor biodegradability, and thus a polyamide having improved biodegradability is demanded.

In view of the foregoing, an object of the present invention is to provide a polyamide having functions such as a high refractive index, high strength, and biodegradability.

DISCLOSURE OF THE INVENTION

In order to overcome the aforementioned drawbacks, the present inventors have conducted extensive studies on dicarboxylic acids which can serve as raw materials for producing polyamides, and have found that polyamides which are produced by polycondensing 2H-pyran-2-one-4,6-dicarboxylic acid and a variety of diamines exhibit high mechanical strength and have a high refractive index and polarity and that a 2H-pyran-2-one ring has excellent biodegradability. The present invention has been accomplished on the basis of these findings.

Accordingly, the present invention provides a polyamide having a structural repeating unit represented by formula (1)

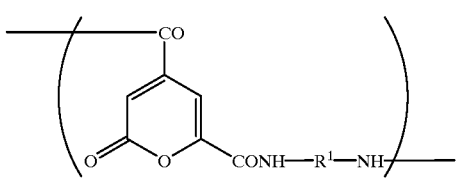
(1)

(wherein $R^1$ represents a divalent hydrocarbon residue optionally having in the structure a heteroatom having no active hydrogen), and a process for producing the same.

The present invention also provides a polyamide having structural repeating units represented by formula (1) and (2):

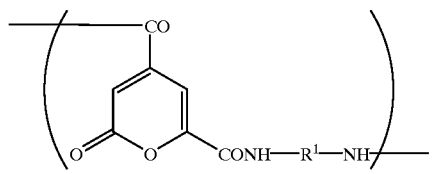
(1)

(2)

(wherein $R^2$ represents a divalent hydrocarbon residue optionally having in the structure a heteroatom having no active hydrogen and $R^1$ represents the same as defined above), and a process for producing the same.

The present invention further provides 2H-pyran-2-one-4,6-dicarboxylic acid derivatives represented by formula (3):

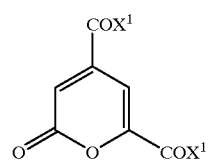
(3)

(wherein $X^1$ represents an alkoxy group or a halogen atom). Among the monomers for producing the polyamide of the present invention, the above carboxylic acid derivatives are novel compounds.

BEST MODES FOR CARRYING OUT THE INVENTION

The polyamides of the present invention have a structural repeating unit represented by formula (1) or structural repeating units represented by formulas (1) and (2). In formulas (1) and (2), each of $R^1$ and $R^2$ represents a divalent hydrocarbon residue optionally having in the structure a heteroatom having no active hydrogen. Among divalent hydrocarbon residues, preferred are $R^3$ and $R^3$—$(OR^3)_1$—, wherein 1 is a number between 1 and 4; and $R^3$ represents a C2–C24 saturated or unsaturated divalent hydrocarbon residue, with a C2–C24 linear chain or branched chain alkylene group, a C3–C8 cycloalkane divalent residue, and a C5–C10 aromatic hydrocarbon divalent residue being particularly preferred. Examples of more preferred $R^1$ and $R^2$ include a trimethylene group, a propylene group, a tetramethylene group, a hexamethylene group, an octamethylene group, a decamethylene group, a dodecamethylene group, a phenylene group, a tolylene group, a xylylene group, a naphthalene group, a cyclohexylene group, and —$CH_2CH_2(OCH_2CH_2)_2$—. These hydrocarbon residues may have a substituent having no active hydrogen such as an alkoxy (preferably C1–C6) group, an alkanoyl (preferably C2–C6) group, an alkyl (preferably C1–C6) group, an aryl (preferably C6–C14) group, or an aralkyl (preferably C7–C18) group.

In the polyamide having structural repeating units represented by formulas (1) and (2), these two types of units may be linked in a block manner (i.e., block copolymer) or randomly (i.e., random copolymer).

No particular limitation is imposed on the molecular weight of the polyamide of the present invention, and it varies in accordance with use. Typically, the molecular weight based on the number average molecular weight is preferably 10,000–200,000, more preferably 40,000–100,000. The molecular weight is particularly preferably 60,000–80,000 in view of moldability from a solution or melt thereof and development of physical properties such as mechanical strength.

The polyamide of the present invention having a structural repeating unit represented by formula (1) may be produced in accordance with the following reaction scheme:

Reaction scheme 1

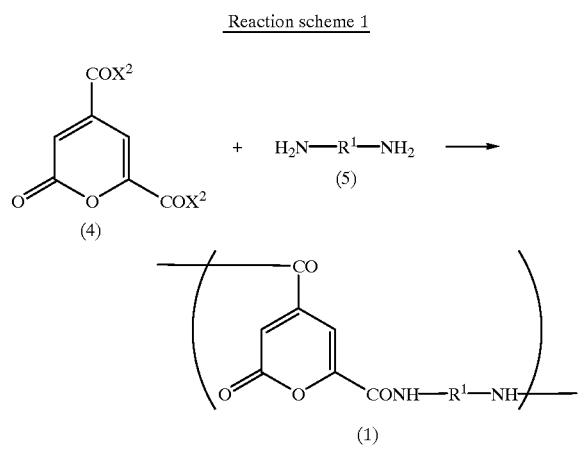

(wherein $X^2$ represents a hydroxyl group, an alkoxy group, or a halogen atom; $R^1$ is the same as defined above).

Specifically, a 2H-pyran-2-one-4,6-dicarboxylic acid derivative (4) and a diamine (5) are subjected to polycondensation reaction, to thereby produce the polyamide of the present invention (1).

Among dicarboxylic monomers (4), a monomer in which $X^2$ is an alkoxy group and a monomer in which $X^2$ is a halogen atom are novel compounds. The compounds can be produced by converting 2H-pyran-2-one-4,6-dicarboxylic acid represented by formula (4) (wherein X is OH) to an ester or an acid halide thereof through a customary method. Among alkoxy groups for $X^2$, a lower alkoxy group is preferred, with a C1–C6 alkoxy group being particularly preferred in view of reactivity to diamines. Among halogen atoms, a chlorine atom and a bromine atom are preferred.

Appropriate types of polycondensation may be employed in accordance with dicarboxylic species (4). For example, dehydration-polycondensation is preferably employed when a dicarboxylic species (4) in which $X^2$ is a hydroxyl group is used. Similarly, alcohol-removing-polycondensation is preferably employed when a dicarboxylic derivative (4) in which $x^2$ is an alkoxyl group is used and interfacial-polycondensation is preferably employed when a dicarboxylic derivative (4) in which $X^2$ is a halogen atom is used.

In dehydration-polycondensation, for example, dicarboxylic acid (4) and a diamine (5) are mixed at a mol ratio of approximately 1:1, and the mixture is heated in the presence of an optional dehydration-condensing agent such as dicyclohexylcarbodiimide.

In alcohol-removing-polycondensation, for example, a dicarboxylic acid diester (4) and a diamine (5) are mixed at a mol ratio of approximately 1:1, and the mixture is heated.

Interfacial-polycondensation is carried out, for example, by employing an interface between a solution of a dicarboxylic dihalide (4) in halohydrocarbon and an aqueous solution containing alkali hydroxide and a diamine (5). Examples of halohydrocarbon include tetrachlorocarbon and chloroform. Sodium hydroxide is preferably used as the alkali hydroxide.

The polyamide of the present invention having structural repeating units represented by formulas (1) and (2) may be produced in accordance with the following reaction scheme:

Reaction scheme 2

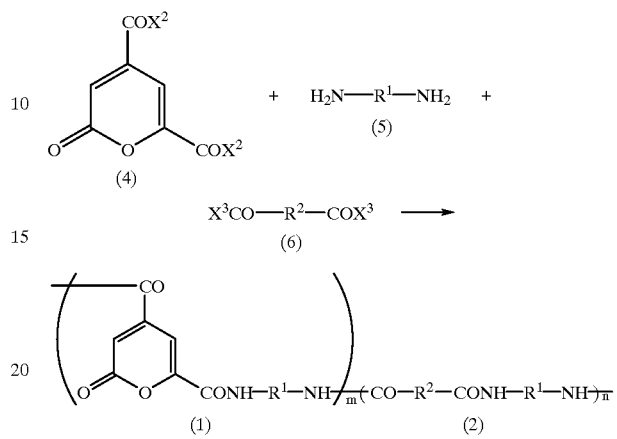

(wherein $X^3$ represents a hydroxyl group, an alkoxy group, or a halogen atom; m and n are integers; and $R^1$, $R^2$, and $X^2$ are the same as defined above).

Specifically, a 2H-pyran-2-one-4,6-dicarboxylic acid derivative (4), a diamine (5), and a dicarboxylic acid derivative (6) are subjected to polycondensation reaction, to thereby produce the polyamide of the present invention having structural repeating units represented by formulas (1) and (2).

Among alkoxy groups for $X^3$ in the dicarboxylic monomer (6), a lower alkoxy group is preferred, with a C1–C6 alkoxy group being particularly preferred in view of reactivity to diamines. Among halogen atoms, a chlorine atom and a bromine atom are preferred.

Appropriate types of polycondensation may be employed in accordance with dicarboxylic species (4) and (6). For example, dehydration-polycondensation is preferably employed when dicarboxylic species (4) and (6) in which each of $X^2$ and $X^3$ is a hydroxyl group are used. Similarly, alcohol-removing-polycondensation is preferably employed when dicarboxylic species (4) and (6) in which each of $X^2$ and $X^3$ is an alkoxyl group are used, and interfacial-polycondensation is preferably employed when dicarboxylic species (4) and (6) in which each of $X^2$ and $X^3$ is a halogen atom are used.

These reactions may be carried out in a manner similar to that employed in the aforementioned reaction scheme 1, except that an arbitrary amount of dicarboxylic acid derivative (6) is added.

The ratio of structural repeating units (1) to (2) (m:n) is preferably 4:1–1:4, with 2:1–1:2 being particularly preferred.

A variety of additives may optionally be added to the polyamide of the present invention. Examples of additives include an anti-oxidant, a colorant, a UV-absorber, a light stabilizer, a silane coupling agent, a storage stabilizer, a plasticizer, a lubricant, a solvent, a filler, an anti-aging agent, a wettability-modifier, and a coatability-modifier.

In the thus-obtained polyamides of the present invention, a 2H-pyran-2-one ring structure imparts rigidity to the polyamides. The polyamides may have a repeating unit combination of "rigid ring unit-soft aliphatic chain unit" or that of "rigid ring unit-rigid aromatic group unit" by selecting $R^1$ and $R^2$. The polyamides having such a structure serve as materials having a wide range of physical properties and are useful as soft, elastic, or high-strength fibers and plastics. In addition, since the 2H-pyran-2-one ring has a high polarity and refractive index, the polyamides of the present invention obtained therefrom also have a high polarity and refractive index and are applicable to fiber for cloth. Furthermore, the 2H-pyran-2-one ring is found in an intermediate product during biodegradation of lignin by wild-type bacteria and is further degraded in soil to produce carbon dioxide and water. Thus, the polyamides of the present invention undergo rapid biodegradation by lignin-degrading wild-type bacteria in soil.

EXAMPLES

The present invention will next be described in more detail by way of examples, which should not be construed as limiting the invention thereto.

Example 1

In acetonitrile (100 mL), 2H-pyran-2-one-4,6-dicarboxylic acid (hereinafter abbreviated as PDC) (10 g) was dissolved. A mixture of the solution and oxalic dichloride (20 mL) was allowed to react at room temperature for 20 hours. The reaction mixture was dried under reduced pressure and purified through sublimation at 120° C and approximately 0.1 mmHg, to thereby produce 8.2 g of a corresponding acid chloride, 2H-pyran-2-one-4,6-dicarboxylic dichloride (hereinafter abbreviated as PDC chloride), in the form of white needle-like crystals.

($^1$H-NMR: in $d_3$-acetonitrile) PDC: 7.1, 7.4 (ring proton), 1.43 (—COOH), PDC chloride: 7.4, 7.6 (ring proton)

($^{13}$C-NMR: in $d_3$-acetonitrile)

PDC: 145, 152 (>$\underline{C}$—COOH), 108, 122 (ring carbon, unsubstituted), 161, 165 (carbonyl and —COOH), PDC chloride: 145, 150 (>$\underline{C}$—COOH), 110, 128 (ring carbon, unsubstituted), 164 (ketone), 157, 160 (—COCl) ppm.

(IR)

PDC: 3400 (—CO$\underline{OH}$), 1730 (ketone and carboxylic acid), PDC chloride: 1730 (ketone), 1750 (—COCl), 720 (C—Cl) cm$^{-1}$.

Example 2

PDC (10 g) was dissolved in methanol (500 mL), and concentrated hydrochloric acid (1 mL) was added to the solution. The resultant mixture was refluxed by boiling for 24 hours, and then concentrated to 50 mL at ambient temperature under reduced pressure. Chloroform (300 mL) was added to the mixture. The resultant mixture was cooled with ice, and precipitated unreacted PDC was removed through filtration. The filtrate was partitioned by shaking with an 0.5% aqueous solution (100 mL) of sodium bicarbonate and subsequently twice with water (300 mL). The separated chloroform solution was dried over anhydrous sodium sulfate, filtered, and brought to dryness under reduced pressure to thereby obtain 7.8 g of dimethyl 2H-pyran-2-one-4,6-dicarboxylate (hereinafter abbreviated as PDCM).

($^1$H-NMR: in CDCl$_3$) 7.15, 7.5 (ring proton), 3.96 (methyl)

($^{13}$C-NMR: in CDCl$_3$) 54 (methyl), 142, 150 (>$\underline{C}$—COOCH$_3$), 108, 122 (ring carbon, unsubstituted), 163 (ketone), 160 (—COO—) ppm.

(IR) 1730 (ketone), 1750 (ester carbonyl), 1100, 1280 (—C—O—C).

Example 3

PDC chloride (2.00 g, 9.04 mmol) was dissolved in chloroform (30 mL). An aqueous solution (30 mL) containing hexamethylenediamine (1.58 g, 13.6 mmol) and NaOH (0.54 g, 13.6 mmol) was gently poured into the chloroform solution. A stirring paddle disposed at the liquid-liquid interface was rotated at approximately 30 rpm for 10 minutes, collecting formed polyamide film. The thus-formed polyamide film was successively washed with hot water and ethanol and dried, to thereby obtain 2.41 g of a polyamide represented by formula (1) in which R was —(CH$_2$)$_6$— in the form of white powder.

($^1$H-NMR: in $d_7$-DMF) 7.1, 7.5 (ring proton), 8.8 (amido), 4.4 (a-methylene), 3.3 (β-methylene), 1.3 (γ-methylene)

($^{13}$C-NMR: in $d_7$-DMF) 145, 148 (>$\underline{C}$—CONH—), 109, 119 (ring carbon, unsubstituted), 150 (ketone), 160 (amido carbon), 40 (α-methylene), 27 (β-methylene), 14 (γ-methylene) ppm.

(IR) 3280 (>N—H, amido), 1640 (carbonyl), 1685 (amido I), 1540 (amido II), 2920 (methylene, stretching) cm$^{-1}$.

The intrinsic viscosity as measured in formic acid at 25° C. was 1.85 dL/g. The number average molecular weight and weight average molecular weight were 67,000 and 104,000, respectively, as measured by means of GPC by use of poly(N-vinylpyrrolidone) as a standard.

Example 4

The procedure of Example 3 was repeated except that decamethylenediamine (2.33 g, 13. 6 mmol) was used instead of hexamethylenediamine, to thereby obtain 2.73 g of a polyamide represented by formula (1) in which R was —(CH$_2$)$_{10}$— as white powder.

($^1$H-NMR: in $d_7$-DMF)

The peak profile was identical to that obtained in Example 3, except that peaks attributed to methylenic protons of γ- and δ-positions were observed at approximately 1.4 ppm.

($^{13}$C-NMR: in $d_7$-DMF)

The peak profile was identical to that obtained in Example 3, except that peaks attributed to methylenic carbons of γ- and δ-positions were observed at 14–12 ppm.

(IR)

The IR spectrum was very similar to that obtained in Example 3, except that the intensity of a peak attributed to stretching vibration of methylene at approximately 2920 cm$^{-1}$ increased.

The intrinsic viscosity as measured in formic acid at 25° C. was 2.05 dL/g. The number average molecular weight and weight average molecular weight were 96,000 and 147,000, respectively, as measured by means of GPC in a manner similar to that employed in Example 3.

Example 5

The procedure of Example 3 was repeated except that dodecamethylenediamine (2.71 g, 13.6 mmol) was used instead of hexamethylenediamine, to thereby obtain 3.16 g of a polyamide represented by formula (1) in which R was —(CH$_2$)$_{12}$— as white powder.

($^1$H-NMR: in $d_7$-DMF)

The peak profile was identical to that obtained in Example 3, except that peaks attributed to methylenic protons of γ-, δ-, and ε-positions were observed at approximately 1.4 ppm.

($^{13}$C-NMR: in $d_7$-DMF)

The peak profile was identical to that obtained in Example 3, except that peaks attributed to methylenic carbons of γ-, δ-, and ε-positions were observed at 14–11 ppm.

(IR)

The IR spectrum was very similar to that obtained in Example 3, except that the intensity of a peak attributed to stretching vibration of methylene at approximately 2920 cm$^{-1}$ increased.

The intrinsic viscosity as measured in formic acid at 25° C. was 1.94 dL/g. The number average molecular weight and weight average molecular weight were 72,000 and 113,000, respectively, as measured by means of GPC in a manner similar to that employed in Example 3.

Example 6

Into a solution of PDC chloride (2.00 g, 9.04 mmol) in acetonitrile (30 mL), an acetonitrile solution (50 mL) comprising p-phenylenediamine (0.976 g, 9.04 mmol) and triethylamine (0.914 g, 9.04 mmol) was added dropwise over about one hour with cooling with ice. After the mixture was stirred with cooling with ice for two hours, hexamethylphosphoric triamide (hereinafter abbreviated as HMPT) (100 mL) was added to the mixture. The resultant mixture was stirred at room temperature for 12 hours. The whole mixture was put in saturated brine (500 mL). The precipitates were collected, washed with hot water, acetonitrile, and ethanol, to thereby obtain 2.65 g of a polyaramid represented by formula (1) in which R was —(p-C$_6$H$_4$)— as pale yellow powder.

($^1$H-NMR: in d$_7$-DMF) 7.1, 7.5 (proton, PDC ring), 6.2. 6.8 (proton, benzene ring), 9.1 (amido).

($^{13}$C-NMR: in d$_7$-DMF) 145, 148 (>$\underline{C}$—CONH—, PDC ring), 109, 119 (carbon, unsubstituted, PDC ring), 134 (>$\underline{C}$—NHCO—, benzene ring), 121 (carbon, unsubstituted, benzene ring), 150 (ketone), 160 (amido carbon) ppm.

(IR) 3275 (>N—H, amido), 1640 (carbonyl), 1685 (amido I), 1544 (amido II), 3040, 2980 (C—H, benzene ring) cm$^{-1}$.

The intrinsic viscosity as measured in formic acid at 25° C. was 2.20 dL/g. The number average molecular weight and weight average molecular weight were 101,000 and 154,000, respectively, as measured by means of GPC in a manner similar to that employed in Example 3.

Example 7

The procedure of Example 6 was repeated, except that m-phenylenediamine (0.976 g, 9.04 mmol) was used, to thereby obtain 2.07 g of a polyaramid represented by formula (1) in which R was —(m-C$_6$H$_4$)— as pale yellow powder.

($^1$H-NMR: in d$_7$-DMF) 7.1, 7.5 (proton, PDC ring), 6.2, 6.8, 7.2 (proton, benzene ring), 9.1 (amido).

($^{13}$C-NMR: in d$_7$-DMF) 146, 148 (>$\underline{C}$—CONH—, PDC ring), 110, 119 (carbon, unsubstituted, PDC ring), 133 (>$\underline{C}$—NHCO—, benzene ring), 120 (carbon, unsubstituted, benzene ring), 150 (ketone), 162 (amido carbon) ppm.

(IR) 3275 (>N—H, amido), 1640 (carbonyl), 1685 (amido I), 1544 (amido II), 3040, 2980 (C—H, benzene ring) cm$^{-1}$.

The intrinsic viscosity as measured in formic acid at 25° C. was 2.88 dL/g. The number average molecular weight and weight average molecular weight were 125,000 and 168,000, respectively, as measured by means of GPC in a manner similar to that employed in Example 3.

Example 8

An aqueous solution (50 mL) of PDC (2.00 g, 10.86 mmol) and a solution of p-xylylenediamine (1.77 g, 13.0 mmol) in methanol (30 mL) were mixed, to thereby form white precipitates. The precipitates were collected through filtration, washed with water, and dried under reduced pressure, to thereby form 3.08 g (9.63 mmol) of a 1:1 salt thereof. A portion of the salt was dissolved in HMPT (100 mL) to form a suspension. A solution of dicyclohexylcarbodimide (hereinafter abbreviated as DCC) (3.97 g, 19.26 mmol) in HMPT (30 mL) was added to the suspension, and the mixture was allowed to react for 20 hours by heating to 60° C. By-produced dicyclohexyl urea (hereinafter abbreviated as DC urea) was removed through hot-filtration, and the filtrate was poured to methanol (500 mL) while stirring. The formed precipitates were collected through filtration and dried, to thereby obtain 2.44 g of a polyaralkylamide represented by formula (1) in which R was —(p-CH$_2$—C$_6$H$_4$—CH$_2$)— as pale yellow powder.

($^1$H-NMR: in d$_7$-DMF) 7.1, 7.5 (proton, PDC ring), 6.8 (proton, benzene ring), 9.0 (amido), 3.2 (methylene).

($^{13}$C-NMR: in d$_7$-DMF) 145, 147 (>$\underline{C}$—CONH—, PDC ring), 108, 117 (carbon, unsubstituted, PDC ring), 129 (>$\underline{C}$—CH$_2$—, benzene ring), 122 (, carbon, unsubstituted, benzene ring), 150 (ketone), 160 (amido carbon), 64 (methylene) ppm.

(IR) 3275 (>N—H, amido), 1640 (carbonyl), 1684 (amido I), 1546 (amido II), 3038, 2984 (C—H, benzene ring) cm$^{-1}$.

The intrinsic viscosity as measured in formic acid at 25° C. was 1.74 dL/g. The number average molecular weight and weight average molecular weight were 62,000 and 94,000, respectively, as measured by means of GPC in a manner similar to that employed in Example 3.

Example 9

PDCM (2.00 g, 9.43 mmol) and 1,4-cyclohexaneformdiamide (1.60 g, 9.43 mmol) were mixed, and the mixture was allowed to react at 180° C. for 20 hours under nitrogen while by-produced methyl formate was removed through distillation. Solidified polymer was taken by breaking the glass-made reactor, finely crushed by use of a mortar, and washed with hot water and ethanol, to thereby obtain 2.91 g of a polyamide represented by formula (1) in which R was -(1,4-cyclohexylene)- as pale yellow powder.

($^1$H-NMR: in d$_7$-DMF) 7.1, 7.5 (proton, PDC ring), 4.1, 2.4 (proton, cyclohexane ring), 8.8 (amido).

($^{13}$C-NMR: in d$_7$-DMF) 143, 146 (>$\underline{C}$—CONH—, PDC ring), 108, 116 (carbon, unsubstituted, PDC ring), 56, 42 (carbon, cyclohexane ring), 152 (ketone), 161 (amido carbon) ppm.

(IR) 3277 (>N—H, amido), 1641 (carbonyl), 1682 (amido I), 1543 (amido II), 2982 (C—H, cyclohexane ring) cm$^{-1}$.

The intrinsic viscosity as measured in formic acid at 25° C. was 2.09 dL/g. The number average molecular weight and weight average molecular weight were 69,000 and 127,000, respectively, as measured by means of GPC in a manner similar to that employed in Example 3.

Example 10

PDC chloride (0.10 g, 0.45 mmol) and adipic dichloride (0.34 g, 1.84 mmol) were dissolved in chloroform (20 mL)

placed in a 100-mL beaker. Hexamethylenediamine (1.06 g, 9.10 mmol) and $K_2CO_3$ (0.31 g, 2.26 mmol) serving as a dechlorinating agent were dissolved in $H_2O$ (10 mL) placed in a 100-mL beaker. The aqueous solution was gently poured into the chloroform solution. The formed interface was gently stirred so as not to intermingle two layers, and formed solid was collected by means of a stirring paddle. The solid was dispersed in $H_2O$, re-collected through filtration, and dried under reduced pressure, to thereby obtain a copolymer in which $R^1$ was —$(CH_2)_6$— and $R^2$ was —$(CH_2)_4$—. Formation of the copolymer was identified through the following analyses.

(FT-IR) 3320 (NH), 2950 (—$CH_2$—, methylene chain), 1750 (>CO, pyrone ring), 1670 (amido I), 1540 (amido II), 1270 (>CN) cm$^{-1}$ ($^1$H-NMR) 1.5, 3.4 (methylene chain), 7.0, 7.4 (PDC ring), approximately 7.5 (amido, methylene chain), 8.5 (amido, PDC skeleton) ppm (Elemental analysis) C:H:O:N=0.425:0.440:0.076:0.059

(theoretical, 52% of PDC introduction C:H:O:N= 0.43:0.44:0.07:0.06)

The proportion of introduced PDC in the polymer was 52%, which was obtained from elemental analysis and the ratio of the integral height at the peak (approximately 7.5 ppm) attributed to methylene-chain-amido to that (approximately 8.5 ppm) attributed to PDC-skeleton-amido.

Example 11

In a four-neck flask equipped with a stirrer, a nitrogen inlet, a drying tube, and a dropping funnel, a solvent (tetrahydrofuran (20 mL) and acetonitrile (20 mL)), hexamethylenediamine 0.52 g (4.5 mmol), and triethylamine (0.63 mL) were placed. PDC chloride (0.2 g, 0.9 mmol) was dissolved in a solvent (10 mL) identical to the above solvent, and the solution was added dropwise to the above mixture while stirring and cooling with ice. After stirring was completed, a solution of adipic chloride (0.66 g, 3.62 mmol) in the same solvent (10 mL) was further added dropwise, and the reaction mixture was allowed to polymerize for five days. The product was dispersed in $H_2O$ (500 mL), re-collected through filtration, and dried under reduced pressure, to thereby obtain a copolymer in which $R^1$ was —$(CH_2)_6$— and $R^2$ was —$(CH_2)_4$—. Formation of the copolymer was identified through the following analyses.

(FT-IR) 3320 (NH), 2950 (—$CH_2$—, methylene chain), 1750 (>CO, pyrone ring), 1670 (amido I), 1540 (amido II), 1270 (>CN) cm$^{-1}$ ($^1$H-NMR) 1.5, 3.4 (methylene chain), 7.0, 7.4 (PDC ring), approximately 7.5 (amido, methylene chain), 8.5 (amido, PDC skeleton) ppm (Elemental analysis) C:H:O:N=0.477:0.441:0.072:0.058

(theoretical, 48% of PDC introduction C:H:O:N= 0.48:0.44:0.07:0.06)

The proportion of introduced PDC in the polymer was 48%, which was obtained from elemental analysis and the ratio of the integral height at the peak (approximately 7.5 ppm) attributed to methylene-chain-amido to that (approximately 8.5 ppm) attributed to PDC-skeleton-amido.

Example 12

The procedure of Example 11 was repeated, except that hexamethylenediamine (0.52 g, 4.5 mmol), PDC chloride (0.33 g, 1.51 mmol), and adipic chloride (0.55 g, 3.01 mmol) were used, to thereby obtain a copolymer in which $R^1$ was —$(CH_2)_6$— and $R^2$ was —$(CH_2)_4$—. Formation of the copolymer was identified through the following analyses.

(FT-IR) 3320 (NH), 2950 (—$CH_2$—, methylene chain), 1750 (>CO, pyrone ring), 1670 (amido I), 1540 (amido II), 1270 (>CN) cm$^{-1}$ ($^1$H-NMR) 1.5, 3.4 (methylene chain), 7.0, 7.4 (PDC ring), approximately 7.5 (amido, methylene chain), 8.5 (amido, PDC skeleton) ppm (Elemental analysis) C:H:O:N=0.467:0.434:0.092:0.065

(theoretical, 80% of PDC introduction C:H:O:N= 0.47:0.43:0.09:0.07)

The proportion of introduced PDC in the polymer was 80%. which was obtained from elemental analysis and the ratio of the integral height at the peak (approximately 7.5 ppm) attributed to methylene-chain-amido to that (approximately 8.5 ppm) attributed to PDC-skeleton-amido.

Example 13

Acetonitrile employed as a solvent for reaction was pre-dehydrated by use of calcium hydroxide for one night and distillated. Subsequently, the acetonitrile was further distillated in the presence of $P_2O_5$, to thereby prepare a solvent. Distillated 1,2-bis(2-aminoethoxy)ethane (BAE) and triethylamine were employed.

In a four-neck flask equipped with a stirrer, a nitrogen inlet, a drying tube, and a dropping funnel, BAE 0.21 g (2.32 mmol), triethylamine (0.27 g, 2.66 mmol), and acetonitrile (50 mL) were placed. PDC chloride (0.50 g, 2.26 mmol) was dissolved in acetonitrile (50 mL), and the solution was added dropwise to the above mixture while stirring and cooling with ice. The reaction mixture was allowed to polymerize at room temperature for six days. The product was dispersed in $H_2O$ (1000 mL), collected through filtration, and dried under reduced pressure. The dried product was dissolved in a solution of trifluoroacetic anhydride in chloroform, to carry out N-trifluoroacetylation. The product was subjected to two types of reprecipitation, i.e, reprecipitation in methanol or $H_2O$ and reprecipitation in a saturated solution of LiCl in dimethylformamide, two steps being repeated. Thus, 0.62 g of polymer in which $R^1$ was —$CH_2CH_2OCH_2CH_2OCH_2CH_2$— was obtained. Formation of the polymer was identified through the following analyses.

(FT-IR) 3320 (NH), 2950 (—$CH_2$—, methylene chain), 1750 (>CO, pyrone ring), 1670 (amido I), 1540 (amido II), 1270 (>CN) cm$^{-1}$ ($^1$H-NMR) 3.5, 3.4 (methylene chain), approximately 7.0 (PDC ring), 8.5 (amido, PDC skeleton) ppm Example 14

Acetonitrile employed as a solvent for reaction was pre-dehydrated by use of calcium hydroxide for one night and distillated. Subsequently, the acetonitrile was further distillated in the presence of $P_2O_5$, to thereby prepare a solvent. Distillated 1,2-bis(2-aminoethoxy)ethane (BAE) and triethylamine were employed.

In a four-neck flask equipped with a stirrer, a nitrogen inlet, a drying tube, and a dropping funnel, BAE 0.42 g (4.64 mmol), triethylamine (0.54 g, 5.32 mmol), and acetonitrile (50 mL) were placed. PDC chloride (0.50 g, 2.26 mmol) dissolved in acetonitrile (25 mL) and adipic chloride (0.43 g, 2.26 mmol) dissolved in acetonitrile (25 mL) were sequentially added dropwise to the above mixture while stirring and cooling with ice. The reaction mixture was allowed to polymerize at room temperature for six days. The product was dispersed in H₂O (1000 mL), collected through filtration, and dried under reduced pressure. The dried product was dissolved in a solution of trifluoroacetic anhydride in chloroform, to carry out N-trifluoroacetylation. The product was subjected to two types of repreciptation, i.e, reprecipitation in methanol or H₂O and reprecipitation in a saturated solution of LiCl in dimethylformamide, two steps being repeated. Thus, 0.82 g of copolymer in which $R^1$ was —CH₂CH₂OCH₂CH₂OCH₂CH₂— and $R^2$ was —(CH₂)₄— was obtained. Formation of the polymer was identified through the following analyses.

(FT-IR) 3320 (NH), 2950 (—CH₂—, methylene chain), 1750 (>CO, pyrone ring), 1670 (amido I), 1540 (amido II), 1270 (>CN) cm⁻¹

(¹H-NMR) 3.5, 3.4 (methylene chain), approximately 7.0 (PDC ring), 8.5 (amido, PDC skeleton) ppm (Elemental analysis) C:H:O:N=0.321:0.464:0.156:0.058

(theoretical, 35% of PDC introduction C:H:O:N= 0.32:0.46:0.16:0.06)

The proportion of introduced PDC was 35%, which was obtained through elemental analysis.

Test Example 1

Physical properties of polyamides and polyaramids obtained in Examples 3 to 9 were investigated. The results are shown in Table 1.

TABLE 1

| Ex. | Melting point (° C.) | Glass transition temp. (° C.) | Tensile strength[1] (g/D) | Refractive Index[2] | Solubility |
|---|---|---|---|---|---|
| 3 | 172 (decomp.) | 128 | 9.6 | 1.78 | formic acid, trifluoroacetic acid, DMF, HMPT |
| 4 | 164 (decomp.) | 114 | 7.2 | 1.66 | formic acid, DMF, HMPT |
| 5 | 157 | 108 | 6.4 | 1.59 | formic acid, DMF, HMPT |
| 6 | decomposed at 240 | not identified | 18.5 | 1.84 | formic acid, trifluoroacetic acid, (DMF, HMPT) |
| 7 | decomposed at 240 | not identified | 16.2 | 1.83 | formic acid, trifluoroacetic acid, (DMF, HMPT) |
| 8 | 195 (decomp.) | not identified | 14.4 | 1.75 | formic acid, trifluoroacetic acid, (DMF, HMPT) |
| 9 | 180 | 144 | 12.1 | 1.61 | formic acid, DMF, HMPT |

[1]gram/denire
[2]amorphous film, as measured at 20° C. by use of Na-D line

Industrial Applicability

The present invention provides a polyamide having a high refractive index and biodegradability and are useful as soft, elastic, or high-strength fibers and plastics.

What is claimed is:
1. A polyamide having a structural repeating unit represented by formula (1):

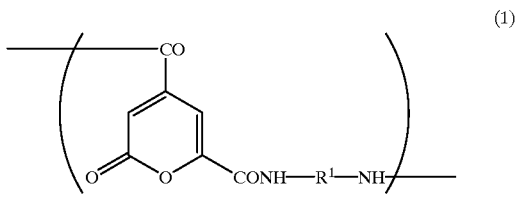

(wherein $R^1$ represents a divalent hydrocarbon residue optionally having in the structure a heteroatom having no active hydrogen).

2. A polyamide having structural repeating units represented by formulas (1) and (2):

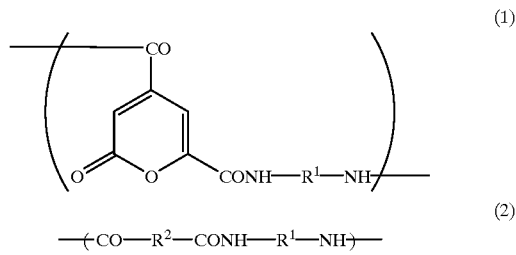

(wherein each of $R^1$ and $R^2$, which may be identical to or different from each other, represents a divalent hydrocarbon residue optionally having in the structure a heteroatom having no active hydrogen).

3. A 2H-pyran-2-one-4,6-dicarboxylic acid derivative represented by formula (3):

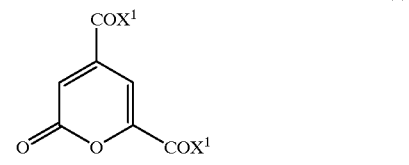

(wherein $X^1$ represents an alkoxy group or a halogen atom).

4. A process for producing a polyamide as described in claim 1, which process comprises polycondensation of a 2H-pyran-2-one-4,6-dicarboxylic acid derivative represented by formula (4):

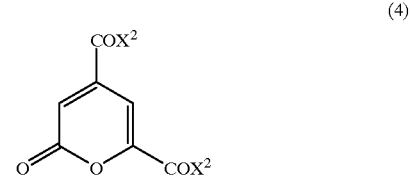

(wherein $x^2$ represents a hydroxyl group, an alkoxy group or a halogen atom) and a diamine represented by H₂N—$R^1$—NH₂ (wherein $R^1$ represents a divalent hydrocarbon residue optionally having in the structure a heteroatom having no active hydrogen).

5. A process for producing a polyamide as described in claim 2, which process comprises polycondensation of a 2H-pyran-2-one-4,6-dicarboxylic acid derivative represented by formula (4):

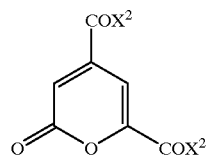

(4)

(wherein $X^2$ represents a hydroxyl group, an alkoxy group or a halogen atom), a diamine represented by $H_2N$—$R^1$—$NH_2$ (wherein $R^1$ represents a divalent hydrocarbon residue optionally having in the structure a heteroatom having no active hydrogen), and a dicarboxylic acid derivative represented by $X^3CO$—$R^2$—$COX^3$ (wherein $R^2$ represents a divalent hydrocarbon residue optionally having in the structure a heteroatom having no active hydrogen, and $X^3$ represents a hydroxyl group, an alkoxy group or a halogen atom).

6. A process according to claim 4 or 5, wherein the polycondensation is interfacial-polycondensation, dehydration-polycondensation, or alcohol-removing-polycondensation.

* * * * *